United States Patent [19]

Knazek et al.

[11] 4,220,725
[45] Sep. 2, 1980

[54] CAPILLARY CELL CULTURE DEVICE

[75] Inventors: Richard A. Knazek; Pietro M. Gullino, both of Bethesda, Md.

[73] Assignee: United States of America, Washington, D.C.

[21] Appl. No.: 892,853

[22] Filed: Apr. 3, 1978

Related U.S. Application Data

[63] Continuation-in-part of Ser. No. 736,451, Oct. 28, 1976, abandoned.

[51] Int. Cl.$^2$ .............................................. C12M 3/04
[52] U.S. Cl. ................................... 435/285; 435/240
[58] Field of Search ............... 195/127, 139; 435/285, 435/286

[56] References Cited

U.S. PATENT DOCUMENTS

3,821,087  6/1974  Knazek et al. ...................... 195/127

Primary Examiner—Alvin E. Tanenholtz
Attorney, Agent, or Firm—Holman & Stern

[57] ABSTRACT

The growth of cells within a device containing a bundle of semi-permeable, tubular capillaries is disclosed. The bundle of capillaries is wrapped in an envelope of porous sheet material, thus creating an extra-envelope space into which the cells can migrate for periodic removal without disturbing the main culture within the capillaries. Porous capillaries may also be employed, in place of or in addition to the porous envelope.

11 Claims, 4 Drawing Figures

CAPILLARY CELL CULTURE DEVICE

BACKGROUND AND SUMMARY OF THE INVENTION

This is a continuation-in-part of U.S application Ser. No. 736,451 filed Oct. 28, 1976 and now abandoned.

The present invention relates to apparatus and a method for growth of living cells. More particularly, the present invention relates to apparatus and a method for cell growth which will allow high density growth of cells while maintaining a stable pericellular environment. The present invention is particularly well suited for growing and maintaining bone marrow in vitro.

Previous attempts to grow cells to densities and/or structures approaching those of living tissues have included various means of supplying nutrient medium to the cells. Such previous methods have included the use of suspension cultures, as well as the use of small pieces of cellulose sponge and various circumfusion techniques.

It has been found that there are certain basic problems which must be overcome in order to grow an organ-like structure in vitro. The first and most obvious problem is that components of the medium must diffuse through the cell layers to reach all cells, and this diffusion, of course, becomes more difficult as the thickness of the cell layer increases.

A second problem associated with growing an organ-like structure in vitro may be the maintainence of a suitable "microenvironment" in conventional cell culture. Thus, the fluid immediately adjacent the growing cell is continuously changing as cellular metabolism proceeds and is returned to its original status only in stepwise fashion when the culture medium is changed or agitated en masse.

A third problem appears to be the requirement for a lattice or suitable material upon which to grow the organ-like structure.

By the present invention, the above and other requirements have been satisfied by apparatus and a method which will allow cells to grow to high density while maintaining a stable pericellular environment.

One known apparatus and method for cell culture on semipermeable tubular members is described in U.S. Pat. Nos. 3,821,087 and 3,883,393. In addition, a known method for growing and maintaining bone marrow in vitro is the Visking membrane dialysis culture reported by D. W. Golde and M. J. Cline in *Blood* 41:45 (1973). The present invention provides an improvement upon these prior art devices by increasing the surface area for nutrient and waste product diffusion to and from the cells located on the outer surface of the capillaries, maintaining a large volume of medium as a nutrient reservoir and waste sink, providing a stable pericellular microenvironment similar to that which exists in vivo, and providing a porous surface either interspersed within or around the nutrient capillaries for cell or virus migration away from the culture. Cells or their particular products are permitted to migrate through the porous envelope or porous capillaries interspersed within the nutrient capillary bundle.

In accordance with the present invention, a plurality of semi-permeable, tubular membranes, hereinafter sometimes referred to as "capillaries", are employed in a bundle which is wrapped in a porous sheath or envelope. This wrapped bundle is positioned within a larger tube or shell having ends adapted for insertion into a perfusion circuit. Inlet ports are provided on the side of the shell for loading cells into the interior of the shell. The ends of the capillaries are secured in end pieces within each end of the shell so that perfusate may be applied to one end of the capillary bundle and flow only through the capillaries without inducing bulk flow in the extracapillary space or the extra-envelope space. Porous capillaries may also be employed, in place of or in addition to the porous envelope.

BRIEF DESCRIPTION OF THE DRAWINGS

The advantages and features of the present invention will be more fully understood from the following description of the preferred embodiments, taken in conjunction with the accompanying drawings, wherein.

DESCRIPTION OF THE PREFERRED EMBODIMENTS

Figure 1:
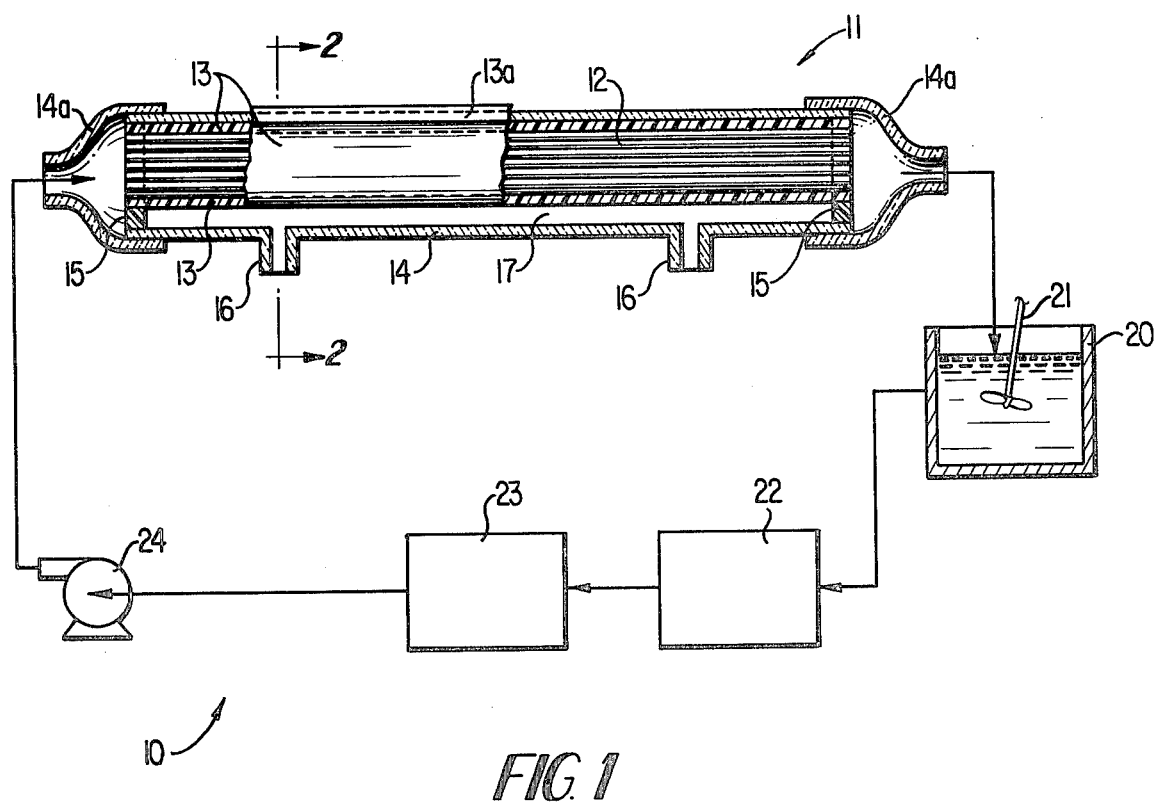
FIG. 1 is a schematic diagram of a system of growing cells on capillaries according to the present invention.
Figure 2:
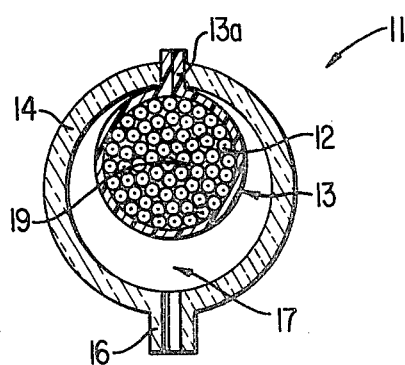
FIG. 2 is a vertical cross-sectional view of a cell culture unit of the present invention, taken along line 2—2 of FIG. 1.

In the illustrated embodiment of the present invention as shown in FIGS. 1 and 2, apparatus 10 is provided for growing cells on capillaries. The apparatus 10 includes one or more cell culture units 11 containing at least one capillary 12 constructed of semi-permeable material. A plurality of capillaries 12 is preferably employed in each cell culture unit 11. Such a plurality of capillaries, which together form a bundle, produces a system which simulates a vascular network within living tissue. The bundle of capillaries is wrapped in a sheath or envelope 13 of porous sheet material. The capillaries 12 are semi-permeable membranes in the form of tubes, as previously discussed.

The capillaries 12 may be formed of any of a variety of semi-permeable materials, including cellulosic or other polymeric materials, particularly semi-permeable cellulose acetate membranes fashioned into hollow, tube-shaped fibers, and also silicone polycarbonate materials and the capillaries may be coated with collagen or other substances to improve cellular adherence, growth, and/or maintainence. Capillaries of different materials may often be advantageously employed within a single unit 11 to improve the passage of oxygen into the cells. The capillary materials are described in more detail in U.S. Pat. No. 3,821,087 which is incorporated by reference. Such fibers may, for example, have an inner diameter of 180 to 200 microns, an outer diameter of 230 to 350 microns, and a capability of allowing passage through the walls of substances having molecular weight of up to about 30,000, or even up to about 100,000, as described in U.S. Pat. No. 3,821,087.

The bundle of capillaries 12 provides a matrix on which cells are permitted to grow. Variation may be made in capillary structure or composition in order to limit the size of molecules which diffuse through the capillary walls and thus provide selectivity as to the components to be made available to the cells or the products to be removed.

The medium employed to provide nutrients for cell growth may be any suitable composition which will make available the nutrients which the cells need for growth and/or function. In general, the choice of the medium will depend upon the cell type being employed at a particular time.

Each capillary should preferably have a diameter small enough that a group bundled together will provide a large surface area so that significant quantities of cells may be grown in a small volume. The diameter of the capillaries should preferably be small enough that when bundled together, a cell growing on any of the capillaries which has reached the limiting diffusive length of the nutrient supply and product removal afforded by that capillary will then come within the radius of influence of one or more adjacent capillaries. The depth to which the cells will grow is limited by the distance to which nutrients or toxic products can travel to or from the cells. Providing more than one capillary in proximity to a cell therefore increases the availability of nutrients and waste removal, thus improving the chances for survival, growth and function of the cell.

The capillaries 12, typically of a length of about 3 to 4 inches, having been wrapped or encased in the envelope 13, are inserted into the unit shell 14 which is formed of glass, polycarbonate or a similar inert material. The ends of these members 12 are secured in end pieces 15 formed of catalyzed monomer, epoxy resin or other suitable sealing material at each end of the shell 14 so that a liquid nutrient medium flowing into an end cap 14a of the cell culture unit 11 will pass through the capillaries 12 and exit through the opposite end cap 14a of the unit 11, without inducing bulk flow in the extra-capillary space 19 within the envelope 13 or in the extra envelope space 17.

The use of the envelope 13 to encase the capillaries 12 provides an extra-envelope space 17 within the shell 14 in addition to the extra-capillary space 19 which is provided between the capillaries 12 within the envelope 13. The envelope 13 may be secured to the upper interior surface of the shell 14 by any suitable means such as, for example, extending the envelope material 13 between semi-cylindrical portions of the shell 14, as shown in FIG. 2, and joining the two portions of the shell 14 together so that the upper end portion 13a of the envelope 13 is effectively secured therebetween. The envelope may also be secured only at both end pieces 15. The membrane envelope 13 may be formed of any suitable porous, non-toxic membrane material. Generally, a material having a pore size of approximately 0.1 to 10 microns in diameter is employed. One such membrane which has been employed with good results is a polycarbonate film manufactured by Nuclepore Corporation, Pleasanton, Calif., having a thickness of approximately 5 to 10 microns and with a pore size of about 3 microns in diameter.

As shown in FIG. 1, the perfusing medium which flows through the capillaries 12 may be provided by a system such as that described in U.S. Pat. No. 3,821,087, including a reservoir 20 supplied with a paddle 21 for the perfusing medium and an oxygenator 22 for a gas transfer into the medium. The perfusing medium is preferably exposed to a suitable mixture of $CO_2$ in air or oxygen prior to being pumped through the capillaries 12. A mixture of 5 percent $CO_2$ in air has been used. A pH meter or other detection device 23 may be connected in the line to provide a continuous on-line reading of pH values or other chemical concentrations at the entrance to and/or exit from the unit 11 and a pump 24 provides suitable perfusate flow rates.

Prior to operation, the entire system 10 is sterilized by, for example, ethylene oxide for 6 hours, exposed to air for from one to two days and then flushed with sterile nutrient medium for from one to two days to remove any residual traces of ethylene oxide. The apparatus 10 can be operated in an incubator at about 37° C. and near 100 percent humidity.

In operation, cells suspended in a nutrient medium are introduced into the culture unit 11 by the use of a small hypodermic needle (not shown). The hypodermic needle is employed to inject cells through a septum (not shown) covering the loading ports 16 into the extra-capillary space 19 between capillaries 12, with the needle penetrating the porous membrane envelope 13. The cells are thus allowed to settle onto the capillaries 12 that are continuously perfused by an oxygenated nutrient medium.

During operation, mature blood cells or viral particles, for example, can migrate away from the capillary bundle 12 through the pores of the envelope 13 and fall into the extra-envelope space 17 within the shell 14 from which they may be removed periodically without disturbing the main culture within the capillaries 12. Perfusion medium is changed periodically to remove waste products and replenish nutrients.

EXAMPLE 1

A Nuclepore membrane envelope 13 having a 3 micron pores was wrapped around a capillary bundle 12 and then sealed along its longitudinal seam using an ethylene chloride solvent prior to its insertion into a polycarbonate shell 14 and securing the bundle and envelope to the end pieces 15. Human bone marrow was injected through the loading ports 16, piercing the envelope 13 by the use of a fine hypodermic needle. Sixteen days later the capillary bundle 12 and its contents were fixed in formalin and sectioned for histologic study. It was found that nucleated cells were adherent to and formed a fine network between some of the capillaries. No red blood cells were adherent to the capillaries but rather had pooled on the surface of the membrane envelope. Without the membrane, these non-adherent cells would have fallen from the capillaries, out of the radius of effective nutrition afforded by these capillaries, and died. It is uncertain whether or not the red blood cells were newly formed or were present when the marrow was inoculated into the extra-capillary space. However, the red blood cells appeared extremely healthy for being in culture for 16 days. Since the marrow culture did not form a strong extracapillary matrix as do the established cell lines when cultured in the capillary devices, the membrane envelope also serves to hold the fibers in place during the fixation process without resorting to an embedding material, such as agarose, which would dislodge such poorly adherent cells.

It has also been found that migratory cells and cell particles, such as viruses, may pass through such a sheath of porous, non-toxic membrane as that employed for the envelope 13. These may then be recovered by flushing them away from the main bundle of capillaries without dislodging the cells adhering to the capillaries by perfusing the space around the membrane 13 through the loading ports.

As an alternative embodiment, porous capillaries may be added to and form a part of the above-described nutrient capillary bundle 12, in place of or in addition to the porous envelope 13. The porous capillaries would permit the large molecules, viruses, or cells to diffuse into the perfusion medium flowing within the capillaries, or to a collection vial, if attached by a separate collecting system, rather than diffusing into the extra-envelope space 17. The porous capillaries should be non-cytotoxic and may be of any suitable material. For example, cellulosic capillaries from the Millipore Corporation have been used. These capillaries are about 2 mm in diameter and have a pore size of about 0.45 microns in diameter. Such porous capillaries have previously been used clinically to provide an uninterrupted channel for nerve regeneration in hand injuries. Other such porous capillaries having diameters ranging from 1-10 mm and having pore diameters of about 0.1 to 10 microns may also be used.

Figure 3:
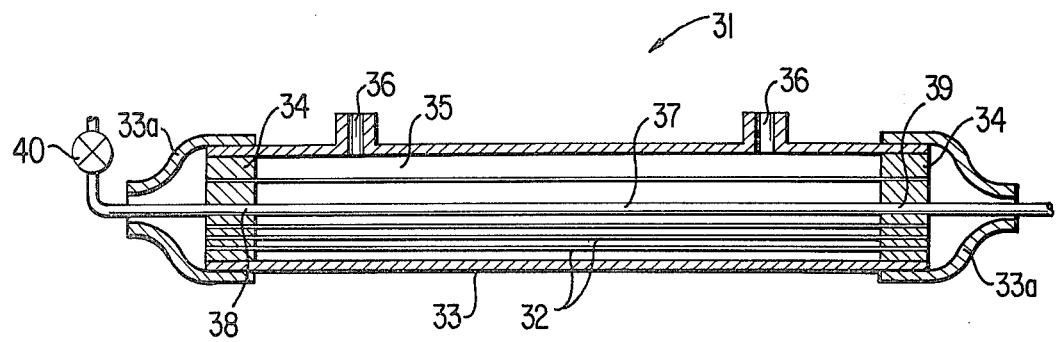
FIG. 3 is a schematic diagram of an alternative embodiment of the present invention.

In FIG. 3, there is shown an embodiment of the present invention in which the apparatus includes a cell culture unit 31 having a plurality of capillaries 32 which may be of a semi-permeable material, such material being the same as described in connection with the capillaries 12 of FIGS. 1 and 2. The capillaries 32 are inserted into the shell 33 and secured in end pieces 34 in a bundled configuration in a manner similar to that previously described for capillaries 12, so that a liquid nutrient medium flowing through into an end cap 33a of the cell culture unit 31 will pass through the capillaries 32 and exit through the opposite end cap 33a without inducing bulk flow in the extra-capillary space 35. Loading ports 36 are provided for the unit 31, and additional components (not shown) for providing the perfusing medium may be connected as a system, in a manner similar to that shown in FIG. 1.

The cell culture unit 31 also includes a porous capillary 37 having one end 38 thereof embedded in the end piece 34 and connected to a valve 40. The other end 39 of the capillary 37 is secured in the end piece 34 and remains open in fluid communication with the perfusing medium passing through the system. The ends 38,39 extend outwardly from the unit 31 and are connected to a separate perfusion circuit and collection system (not shown). The valve 40 is employed to control the liquid nutrient medium flowing through the porous capillary 37. Alternatively, the end 38 of the capillary 37 may be occluded or blocked off in the end piece 34 so as to block the end 38, but without the valve 40 or separate perfusion circuit. In such alternative embodiment, the open end 39 is then in fluid communication with the medium flowing through the other capillaries 32. In the use of such alternative, the open end 39 is preferably positioned at the exit end relative to the flow of nutrient medium through the unit 31.

Figure 4:
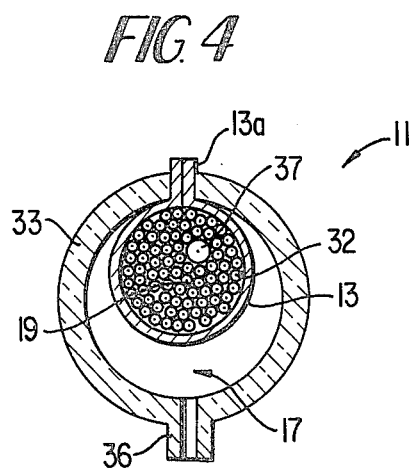
FIG. 4 is a vertical cross-section of a further embodiment of the invention.

In FIG. 4, there is shown an alternative embodiment similar to that of FIG. 3, but wherein the capillaries 32 and porous capillary 37 are bundled in a porous envelope 13, of the type previously described. The arrangement of the valve 40 and separate perfusion circuit, or the alternative occluded end 38, may be essentially the same as described in connection with FIG. 3. The extra-envelope space 17 and extra-capillary space 19 are as described in connection with FIG. 2.

The following example describes a specific cell culture unit 31 which was constructed in accordance with FIG. 3.

EXAMPLE 2

A capillary cell culture unit 31 was constructed, including capillaries 32 which included 90 silicone polycarbonate fibers and 60 XM-50 (Amicon Corporation) fibers. The porous capillary 37 was a CH0020040 tube manufactured by the Millipore Corporation, having a diameter of 2 mm, constructed of cellulose acetate and permeated with 0.22 micron pores. This unit 31 was employed in a method in which Vero cells (African green monkey kidney cells) were inoculated into the extra-capillary space 35.

The use of such porous capillaries would result in increased surface area and improved proximity of the porous surface for cellular or particle egress from the capillary network. Thus, in addition to accumulating in the extra-envelope space 17, the migrated cells, particles, or large molecules would also be allowed to accumulate in the perfusate space within the porous capillaries and be more accessible for harvest.

A primary advantage of the use of the porous capillaries would be to provide a means of exit for otherwise poorly- or non-diffusible cell products away from the extra-capillary space 19 or 35. Such an embodiment would be particularly useful when it is desirable to harvest or remove these products from the vicinity of the cells. For example, certain cells secrete a virus, which if present in high concentration in the vicinity of the cell mass may be toxic or alter cellular behavior. Since viruses, when produced in vivo, can diffuse away from the production cell, this problem does not usually exist in vivo.

An additional factor to be considered is that cells may need the three dimensional structure for expression of certain types of virus production but then there must be a way for these viral particles to escape from the cellular microenvironment. The present invention would appear to provide such a possibility.

The present invention may be advantageously used with the porous capillaries in the culture of undifferentiated parent cells to produce end-of-the-line differentiated cells. In the case of bone marrow, the parent cells or "stem" cells do not migrate out at the marrow cavity whereas their offspring, the red blood cells, white blood cells and platelets do migrate from the marrow cavity into the circulation. Their presence close to the stem cell may act as a negative feedback inhibition for further production of these cells or maintenance of the stem cells in vitro. Providing the differentiated product cell with the porous pathway in the form of the porous capillaries for escape from the microenvironment of the stem cell would solve this problem and provide a means for harvesting the cells.

In some cases, it may be desirable to have a high ratio of extra-envelope 17 to extra-capillary 19 space to dilute out the feedback effect of the migrated substances, particles, or cells. This could be accomplished, for example, by having relatively few capillaries 12 within the envelope 13 sealed within a shell 14 of large volume.

The envelope 13 will also keep poorly adherent cells in closer contact with the capillaries 12,32 both during inoculation and when the parent cell products are being harvested by flushing the extra-envelope space 17.

It is thought that the invention and many of its attendant advantages will be understood from the foregoing description, and it will be apparent that various changes may be made in the present device without departing from the spirit and scope of the invention or sacrificing its material advantages, the forms hereinbefore described being merely preferred embodiments thereof.

The embodiments of the invention in which an exclusive property or privilege is claimed are defined as follows:

1. A cell culture unit for the formation and maintenance of solid tissues in vitro comprising:
   (a) shell means having spaced end portions and defining an elongated chamber therebetween;
   (b) capillary means simulating a vascular network within said chamber, said capillary means including a multiplicity of individual capillaries extending in substantially parallel relationship to each other within said shell means, at least some of said capillaries having walls which are selectively permeable only to nutrients and/or cell products of up to a molecular weight of 100,000 and at least some of said capillaries having walls which are permeable only to gases;
   (c) an envelope of porous sheet material surrounding said capillary means within said chamber, said chamber being divided by said envelope into an intra-envelope space within said envelope and an extra-envelope space outside said envelope, said intra-envelope space and said extra-envelope space communicating with each other only through the walls of said envelope, said intra-envelope space being divided by the walls of said capillaries into an intra-capillary space and an extra-capillary space communicating with each other only through the walls of said capillaries;
   (d) means communicating with said intra-capillary space for passing perfusate therethrough; and
   (e) means communicating with said extra-capillary space for seeding cells and/or retrieving cells or cell products therefrom.

2. The cell culture unit of claim 1, wherein the envelope is formed of a material having a pore size of approximately 0.1 to 10 microns in diameter.

3. The cell culture unit of claim 1, wherein at least one of said capillaries is more porous than the others, said capillary which is more porous having a pore size of about 0.1 to 10 microns in diameter.

4. The cell culture unit of claim 3, wherein said more porous capillary is connected to a separate perfusion circuit, with valve means for controlling the flow through said more porous capillary.

5. The cell culture unit of claim 3, wherein said more porous capillary has one end thereof occluded so as to prevent flow therethrough.

6. The cell culture unit of claim 1 and further including means communicating with said extra-envelope space for retrieving cells and/or cell products therefrom.

7. The cell culture unit of claim 1 wherein the means communicating with said intra-capillary space passes perfusate having nutrients useable by the cells through at least a portion of the capillaries.

8. The cell culture unit of claim 1 wherein upper portions of the envelope are attached to upper interior wall portions of the shell means, thereby to provide a major portion of the extra-envelope space below the lower portions of the envelope.

9. A cell culture unit for the formation and maintenance of solid tissues in vitro comprising:
   (a) shell means having spaced end portions and defining an elongated chamber therebetween;
   (b) capillary means simulating a vascular network within said chamber, said capillary means including a multiplicity of individual capillaries extending is substantially parallel relationship to each other within said shell means, at least some of said capillaries having walls which are selectively permeable only to nutrients and/or cell products of up to a molecular weight of 100,000 and at least some of said capillaries having walls which are permeable only to gases; said chamber being divided by the walls of said capillaries into an intra-capillary space and an extra-capillary space communicating with each other only through the walls of said capillaries, and at least one of said capillaries being more porous than the others, said capillary which is more porous having a pore size of about 0.1 to 10 microns in diameter;
   (c) means communicating with said intra-capillary space for passing perfusate through at least a portion of the capillaries;
   (d) means communicating with said extra-capillary space for seeding cells and/or retrieving cells or cell products therefrom; and
   (e) means for stopping flow of perfusate through said more porous capillary independently of said means for passing perfusate.

10. The cell culture unit of claim 9, wherein said more porous capillary is connected to a separate perfusion circuit, with valve means for controlling the flow through said more porous capillary.

11. The cell culture unit of claim 9, wherein said more porous capillary has one end thereof occluded so as to prevent flow therethrough.

* * * * *